United States Patent
Kumar (10) Patent No.: US 9,921,156 B2
(45) Date of Patent: Mar. 20, 2018

(54) SYSTEM AND METHOD FOR FLUORESCENCE DETECTION

(71) Applicant: Anand T. N. Kumar, Boston, MA (US)

(72) Inventor: Anand T. N. Kumar, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/765,690

(22) PCT Filed: Jan. 31, 2014

(86) PCT No.: PCT/US2014/014007
§ 371 (c)(1),
(2) Date: Aug. 4, 2015

(87) PCT Pub. No.: WO2014/121003
PCT Pub. Date: Aug. 7, 2014

(65) Prior Publication Data
US 2015/0377783 A1 Dec. 31, 2015

Related U.S. Application Data

(60) Provisional application No. 61/760,216, filed on Feb. 4, 2013.

(51) Int. Cl.
*G01N 21/64* (2006.01)
*G01N 33/483* (2006.01)

(52) U.S. Cl.
CPC ..... *G01N 21/6408* (2013.01); *G01N 33/4833* (2013.01); *G01N 2021/6439* (2013.01);
(Continued)

(58) Field of Classification Search
CPC .......... G01N 2021/6439; G01N 21/64; G01N 21/6408; G01N 2201/06113; G01N 2201/12; G01N 33/48; G01N 33/4833
(Continued)

(56) References Cited

U.S. PATENT DOCUMENTS

| 2004/0007675 A1* | 1/2004 | Gillispie | G01J 3/4406 250/458.1 |
| 2004/0015062 A1 | 1/2004 | Nziachristors et al. | |

(Continued)

OTHER PUBLICATIONS

International Search Report and Written Opinion dated May 21, 2014 in connection with PCT/US2014/014007.

(Continued)

*Primary Examiner* — Maureen Wallenhorst
(74) *Attorney, Agent, or Firm* — Quarles & Brady LLP (57) ABSTRACT

A system and method for determining fluorescence decay in a biological sample is provided. The method includes acquiring optical signal data from at least a part of a biological sample undergoing fluorescence, assembling the optical signal data into a set of spatial time-series data, and converting the set of spatial time-series data into a set of spatial frequency time-series data. The method also includes applying a spatial filter to the set of spatial frequency time-series data to yield a set of filtered frequency-series data, the spatial filter configured to separate, from the set of frequency-series data, fluorescence signals consistent with a non-diffuse component and converting the set of filtered frequency-series data into a set of filtered time-series data. The method further includes determining, using the filtered time-series data, a fluorescence signature consistent with fluorescence decay of at least one fluorophore, and generating a report indicative of the fluorescence signature of the biological sample.

35 Claims, 7 Drawing Sheets

(52) U.S. Cl.
CPC ............. *G01N 2201/06113* (2013.01); *G01N 2201/12* (2013.01)

(58) Field of Classification Search
USPC ............ 436/63, 164, 172; 422/82.05, 82.08; 435/29, 288.7; 702/19
See application file for complete search history.

(56) References Cited

U.S. PATENT DOCUMENTS

| | | | |
|---|---|---|---|
| 2006/0039593 A1 | 2/2006 | Sammak et al. | |
| 2006/0146331 A1* | 7/2006 | Granot | A61B 5/0059 356/432 |
| 2006/0184043 A1 | 8/2006 | Tromberg et al. | |
| 2009/0095911 A1 | 4/2009 | Kim et al. | |
| 2010/0220903 A1 | 9/2010 | May et al. | |
| 2010/0305454 A1 | 12/2010 | Dvorsky et al. | |
| 2011/0164218 A1* | 7/2011 | Ornberg | A61B 3/10 351/206 |
| 2014/0118524 A1* | 5/2014 | Munck | G01N 21/6408 348/79 |

OTHER PUBLICATIONS

Cubedu et all, "Time-resolved imaging in biology and medicine," Journal of Physics D: Applied Physics, vol. 35, No. 9, p. R71-R76; Apr. 18, 2012.

* cited by examiner

SYSTEM AND METHOD FOR FLUORESCENCE DETECTION

CROSS-REFERENCE TO RELATED APPLICATIONS

This application represents the national stage entry of PCT International Application No. PCT/US2014/014007 filed Jan. 31, 2014, which claims the benefit of U.S. Provisional Application Ser. No. 61/760,216, filed Feb. 4, 2013, the disclosures of which are incorporated by reference here in their entirety for all purposes.

GOVERNMENT RIGHTS

This invention was made with government support under grant No. R01EB015325 awarded by the National Institute of Health. The government has certain rights in the invention.

BACKGROUND

The present disclosure relates generally to systems and methods for functional imaging, and, in particular, to systems and methods for fluorescence imaging in turbid media.

Imaging based on fluorescence provides a powerful tool for non-invasive diagnosis of disease in living animals or human subjects, as well as facilitates investigations into many biological processes In fluorescence, incident excitation photons of appropriate wavelengths are absorbed by a sample including fluorescent molecules, or fluorophores, which then emits light at wavelengths that depend upon the energy level arrangement of each fluorophore. On account of a high specificity, fluorescence imaging permits functional contrast resulting from both intrinsic auto-fluorescence and extrinsic fluorescence, using both absorption and emission characteristics unique to particular molecular structures. When appropriately generated and analyzed, optical signals can provide valuable information with respect to the fluorophores embedded in a turbid medium, such as environment, location, or distribution, as well as a contrast between species with different emission spectra. As such, development of disease-specific fluorescent markers and genomic reporters has prompted many concurrent advances in optical imaging techniques using fluorescence.

Fluorescence imaging techniques are, in general, confounded by several factors. First, typical fluorophores include a small Stokes shift, which describes the separation between absorption and emission spectra peaks. Usually optimal detection of fluorescence necessitates choosing filter wavelengths very close to those of the excitation. Coupled with the poor rejection ratio of typical emission filters, this implies a significant leakage of the excitation signal into the fluorescence signal. In the case that fluorophore signal is very intense, this is may not be a major concern. However, since a majority of fluorophores have a low emission quantum yield, which describes the conversion efficiency from excitation to fluorescence, fluorescence signals can be easily overwhelmed by the excitation signal, if the latter is not filtered out efficiently.

A second confounding factor includes the measurement of intrinsic fluorescence lifetimes of fluorophores embedded in scattering tissue. Optical signal detection techniques typically involve three main approaches, namely time-domain (TD) detection using pulsed sources (typically in the femtosecond to pico-second pulse duration range), frequency-domain (FD) detection using modulated sources (typically in the MHz frequency range) and continuous wave (CW) detection using steady state light sources. Of these, the TD approach is most comprehensive since short pulsed sources contain all modulation frequencies, including the zero-frequency component, and facilitate direct lifetime estimation by fitting a decay portion of a spatio-temporal optical signal. By contrast, FD techniques require reconstruction algorithms to recover the true lifetime.

However, even for measurement approaches using TD, unless the temporal decay time constant (lifetime) of fluorescence is longer than about one nano-second (equivalent to intrinsic diffusion timescales), decay times are affected by the optical properties, such as intrinsic absorption and scattering, of the surrounding turbid medium. Therefore, recovery of fluorophore intrinsic lifetimes becomes ambiguous and necessitates complicated reconstruction algorithms that include inversion of coupled differential equations describing fluorescence propagation in tissue, and may require prior knowledge of tissue absorption and scattering. Such approaches can be ill-posed, and may provide additional complexities.

Therefore, there is a need for systems and methods for detecting fluorescence lifetimes and decay profiles in turbid media.

SUMMARY

The present invention overcomes the aforementioned drawbacks by providing a system and method directed to extracting fluorescence lifetimes from diffuse media. Specifically, the present invention provides a spatial filtering of time-resolved data for direct detection of fluorescence lifetimes, which may be shorter than intrinsic diffuse timescales.

In accordance with one aspect of the disclosure, a method for determining fluorescence decay in a biological sample is provided. The method includes acquiring optical signal data from at least a part of a biological sample undergoing fluorescence, assembling the optical signal data into a set of spatial time-series data, and converting the set of spatial time-series data into a set of spatial-frequency time-series data. The method also includes applying a spatial filter to the set of spatial frequency time-series data to yield a set of filtered spatial frequency time-series data, the spatial filter configured to separate, from the set of spatial frequency time-series data, fluorescence signals consistent with a non-diffuse component and converting the set of filtered spatial frequency time-series data into a set of filtered spatial time-series data. The method further includes determining, using the filtered time-series data, a fluorescence signature consistent with fluorescence decay of at least one fluorophore, and generating a report indicative of the fluorescence signature of the biological sample.

In accordance with another aspect of the disclosure, a system for determining fluorescence decay in a biological sample is provided. The system includes an input designed to receive optical signal data from at least a part of a biological sample undergoing fluorescence and at least one processor configured to assemble the optical signal data into a set of time-series data, and convert the set of spatial time-series data into a set of spatial frequency time-series data. The at least one processor is also configured to apply a spatial filter to the set of spatial frequency time-series data to yield a set of filtered spatial frequency time-series data, the spatial filter configured to separate, from the set of spatial frequency time-series data, fluorescence signals consistent with a non-diffuse component and convert the set of filtered spatial frequency time-series data into a set of filtered spatial time-series data. The at least one processor is further configured to determine, using the filtered time-series data, a fluorescence signature consistent with fluorescence decay of at least one fluorophore, and generate a report indicative of the fluorescence signature of the biological sample.

In accordance with another aspect of the disclosure, a method is provided for determining fluorescence decay in a biological sample. The method includes acquiring optical signals from at least a part of a biological sample undergoing fluorescence due to a plurality of fluorophores to assemble a set of spatial time-series data and converting the set of spatial time-series data into a set of spatial frequency time-series data. The method also includes applying a filter to the set of spatial frequency time-series data to yield a set of filtered spatial frequency time-series data, the filter configured to separate, from the set of spatial frequency-time-series data, fluorescence signals consistent with a non-diffuse component and converting the set of filtered spatial frequency time-series data into a set of filtered spatial time-series data. The method further includes determining, using the filtered spatial time-series data, a fluorescence signature consistent with fluorescence decay of the at least one fluorophore in the plurality of fluorophores and generating a report indicative of the fluorescence signature of the biological sample.

The foregoing and other advantages of the invention will appear from the following description.

DETAILED DESCRIPTION

Figure 1:
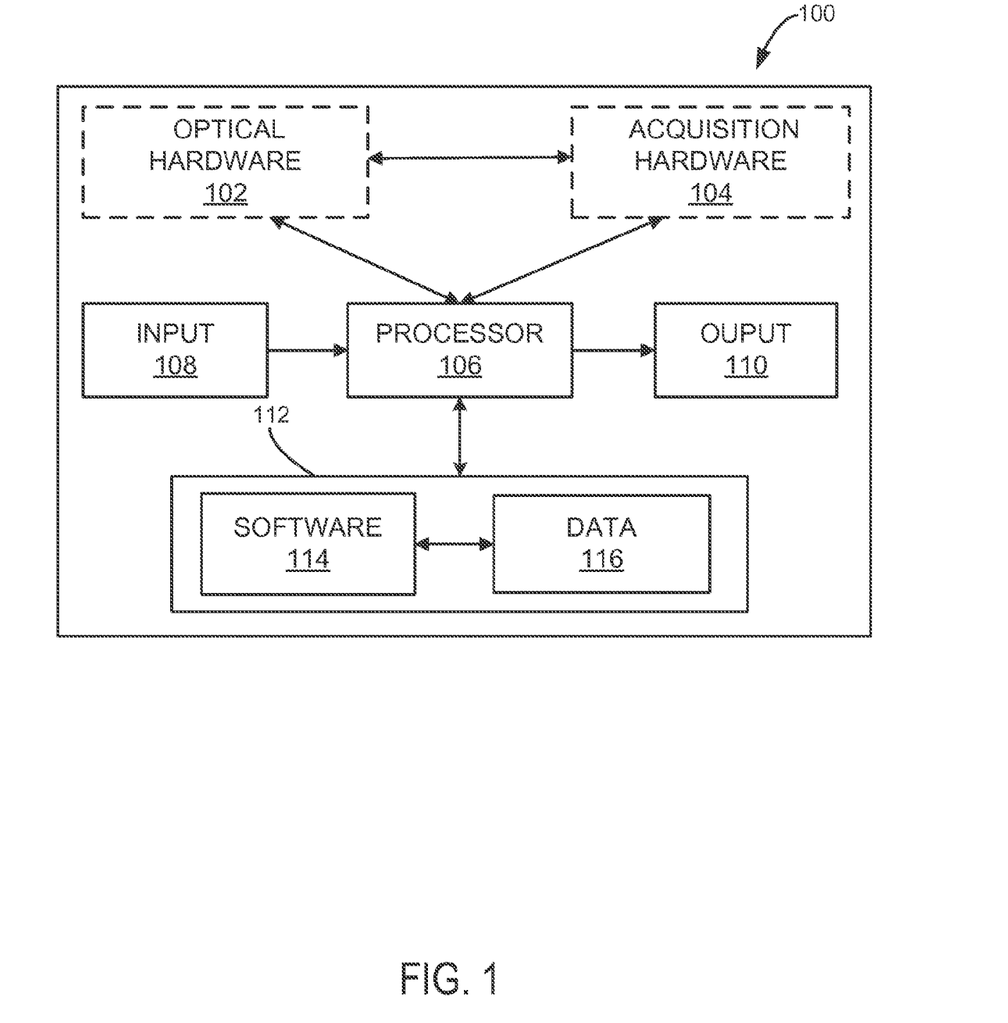
FIG. 1 is a schematic illustration of a fluorescence detection system for use in accordance with the present invention.

Turning to FIG. 1, a block diagram is shown of an exemplary fluorescence system 100, which facilitates fluorescence lifetime detection in turbid medium. The fluorescence system 100 generally may include optical hardware 102, acquisition hardware 104, at least one processor 106, an input 108, an output 110, a memory 112, and any device for reading computer-readable media (not shown). The fluorescence system 100 may be, for example, a workstation, a notebook computer, a personal digital assistant (PDA), a multimedia device, a network server, a mainframe or any other general-purpose or application-specific computing device. The fluorescence system 100 may operate autonomously or semi-autonomously, or may read executable software instructions from a computer-readable medium (such as a hard drive, a CD-ROM, flash memory and the like), or may receive instructions from a user, or any another source logically connected to computer or device, such as another networked computer or server. In one embodiment, the fluorescence system 100 may be configured to acquire and process optical signal data due to fluorescence, and may also be configured to retrieve and process optical signal data already acquired, and stored in any data storage location.

The fluorescence system 100 may include optical hardware 102 configured to induce a fluorescence response in a turbid medium, such as a biological sample or tissue. In some configurations, the optical hardware 102 may include any systems and components capable of delivering, directing and controlling continuous or pulsed light of any desired intensity, duration, wavelength, frequency, polarization, spatial modulation, or pattern, using a single or multiple light sources, configured in accordance with a desired application. Such configurations may be tailored with consideration to specific characteristics of target fluorophore species and surrounding turbid medium, including energy level characteristics, distribution of fluorophores within the medium, optical properties of the medium, fluorophore lifetime, quantum efficiency and so forth. For example, the optical hardware 102 may include light sources or systems designed for producing point-like, spatially modulated, patterned, or time-dependent excitations, or any combinations thereof. In some designs, the optical hardware 102 may also include components or capabilities for filtering light from the single or multiple light sources, configured for use in accordance with a desired application.

The fluorescence system 100 may also include acquisition hardware 104 designed to acquire, either continuously or intermittently, optical signal data from a turbid media undergoing fluorescence, such as a biological sample or tissue, and relay the optical signal data to the processor 106 for processing. In some designs, the acquisition hardware 104 may include features and capabilities for detecting time-domain optical signal data generated using optical hardware 102, as described above, or any other hardware or system designed for inducing fluorescence. Alternatively, acquisition hardware 104 may be configured to detect light from a biological sample or tissue undergoing auto-fluorescence.

The acquisition hardware 104 may be designed to acquire optical signal data using light of any desired intensity, duration, wavelength, polarization, spatial pattern, or modulation. In some configurations, the acquisition hardware 104 may include capabilities for filtering, separating, modifying or intensifying detected light, using any systems or components designed to do so. In addition, some aspects of operation of the acquisition hardware 104 may involve operator direction, input or feedback, or may be performed autonomously by at least one processor 106 in communication with the optical hardware 102, or any other system.

Optical signals resulting from fluorescence response of single or multiple fluorophores, such as fluorescent dyes or fluorescent biological constituents, embedded in, or generally about the turbid medium, may be described by different characteristics, such as quantum yields, decay times or lifetimes. As such, the acquisition hardware 104 may be designed, or directed by the at least one processor 106, to acquire optical signal data consistent with desired time points, segments or portions of any fluorescence response process.

Among the processing tasks for operating the fluorescence system 100, as described, the at least one processor 106 may also be configured to process optical signal data to determine a fluorescence signature consistent with one or more fluorophores. For example, the at least one processor 106 may be designed perform an analysis and processing of the optical signal data in a time-domain or frequency-domain. In some aspects, the at least one processor 106 may be configured to assemble optical signal data into a set of time-series data, which may then be transformed, and filtered, as desired, in a time-resolved fashion, using for example a Fourier and inverse Fourier transformation, and other processing approaches. In some preferred aspects, the at least one processor 106 may be configured to perform a spatial frequency filtering of time-domain fluorescence signals, to separate a non-diffuse component and reject a diffuse component, including a diffuse excitation leakage, facilitating the detection of intrinsic fluorescence lifetimes from turbid media. The basis of this approach is the separation of diffuse fluorescence signals into diffuse and fluorescent component, which may have distinct spatiotemporal behavior.

Using intrinsic fluorescent signals separated by analyzing and processing optical signal data, the at least one processor 106 may be further configured to determine a fluorescence signature by subjecting the intrinsic fluorescent signals to a curve fitting process. The curve fitting process, involving any number of fitting steps, may be performed using any desired time points, segments or portions of a fluorescence response, such as an asymptotic decay behavior. In addition, the at least one processor 106 may be further configured to generate a report indicative of a fluorescence signature from a biological sample or tissue.

The input 108 may take any shape or form, as desired, for operation of the fluorescence system 100, including the ability for selecting, entering or otherwise specifying parameters consistent with operating the fluorescence system 100. In some designs, the input 108 may also be configured to receive optical signal data from systems or hardware designed for acquiring, storing or transmitting optical information from at least a part of a biological sample undergoing fluorescence, and relay the optical signal data to the at least one processor 106 for processing. For example, optical signal data may be obtained by way of systems and methods using wide-field light excitation and detection, such as, digital light projectors (DLP), including any digital micromirror devices, and gated intensified CCD cameras.

The output 110 may take any shape or form, as desired, and may be configured for displaying, among other information, spatiotemporal information related to raw or processed optical signal data. Specifically, the output 110 may provide an indication of a fluorescence signature of any number of fluorophores in a turbid medium. For example, a generated report may be in the form of fluorescence images or fluorescence lifetime maps.

The memory 112 may contain software 114 and data 116, and may be configured for storage and retrieval of processing information and data to be processed by the processor 106. In some aspects, the software 114 may contain instructions directed to performing optical signal data analysis and processing, including separating diffuse fluorescence signals into diffuse and non-diffuse components. In other aspects, the software 114 may include instructions for determining a fluorescence signature using a curve fitting process. The data 116 may take include any data necessary for operating the fluorescence system 100, including raw or processed optical signal data, or data related to optical properties of turbid media, or data needed in the curve fitting process.

Figure 2:
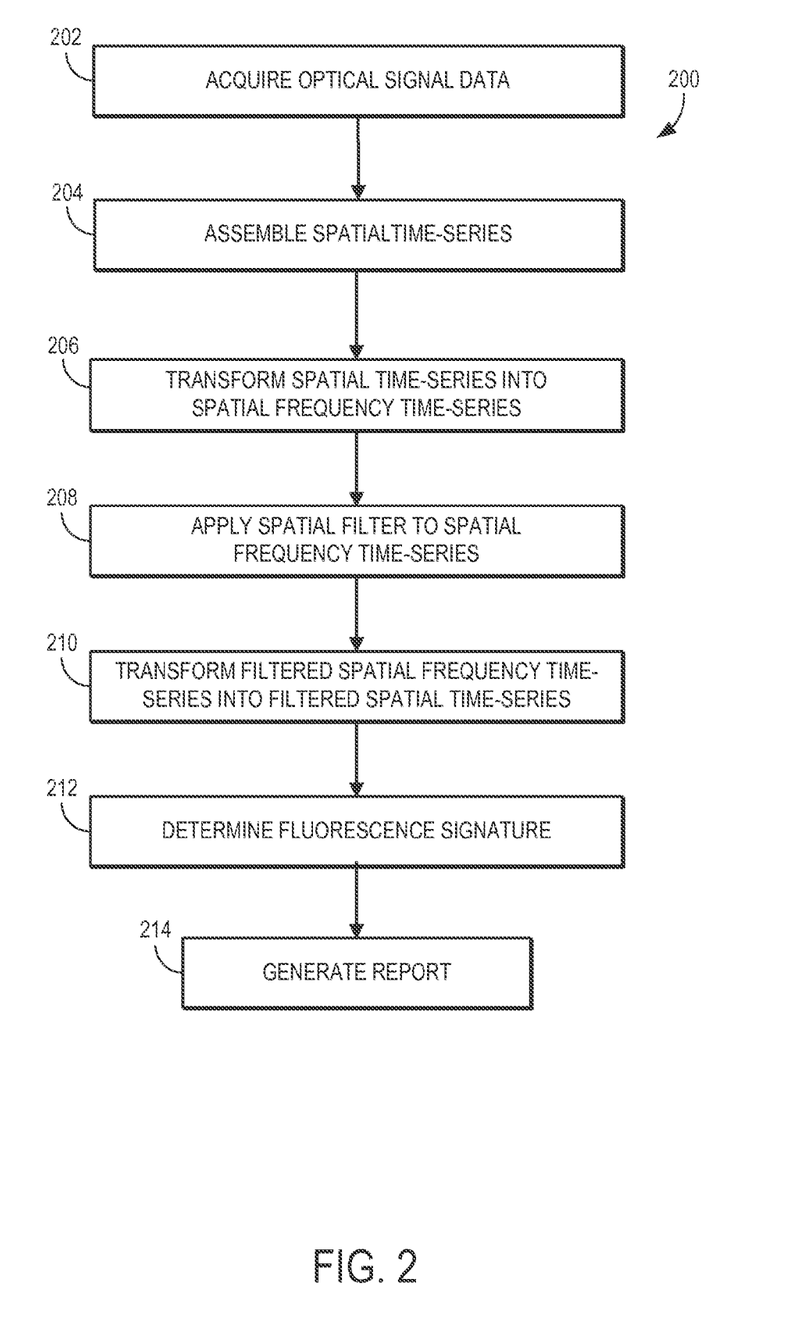
FIG. 2 is a flowchart setting forth the steps of an exemplary method of operating the fluorescence system, such as illustrated in FIG. 1, in accordance with the present invention.

Turning to FIG. 2, an example process 200 setting forth the steps for a mode of operation of the fluorescence system 100 is shown. The process begins at process block 202, where optical signal data from at least one part of a biological sample undergoing fluorescence is acquired, or provided. As described, fluorescence may be induced by using excitation source configured to create an excitation generally point-like, pulsed, patterned, or modulated, or any combination thereof. The optical signal data acquired, or provided, is then assembled in a set of spatial time-series data at process block 204, which is then Fourier transformed for each time point at process block 206 to yield a set of spatial frequency time-series data. In some aspects, at process block 204, the optical signal data may be subject to a threshold processing, for example, using a maximum intensity. The set of spatial frequency time-series data is then spatially filtered at process block 208, using a spatial filter that may be dependent upon a fluorescence decay profile determined by optical properties of the biological sample or tissue. The set of filtered spatial frequency time-series data is then transformed back to the space domain using an inverse Fourier transform at process block 210. The resulting set of filtered time-series data may then be then used at process block 212 to determine a fluorescence signature consistent with fluorescence decay of fluorophores in a turbid medium. This step may include a curve fitting process, in dependence of a spatio-temporal fluorescence response by any single or multiple fluorophores, including an asymptotic decay behavior. This approach may facilitate a reduction, minimization or elimination of a diffuse component from fluorescence signals and may also allow the extraction of fluorescence decay, or lifetime from at least one fluorophore, which in some cases may be shorter than an intrinsic temporal response of a diffuse medium. Then at process block 214, a report of any desired shape or form is generated, the report being indicative of a fluorescence signature in the turbid medium. In some aspects, the report may include single or multiple fluorescence images or fluorescence lifetime maps, depending on the number of fluorescent species of interest.

Figure 3:
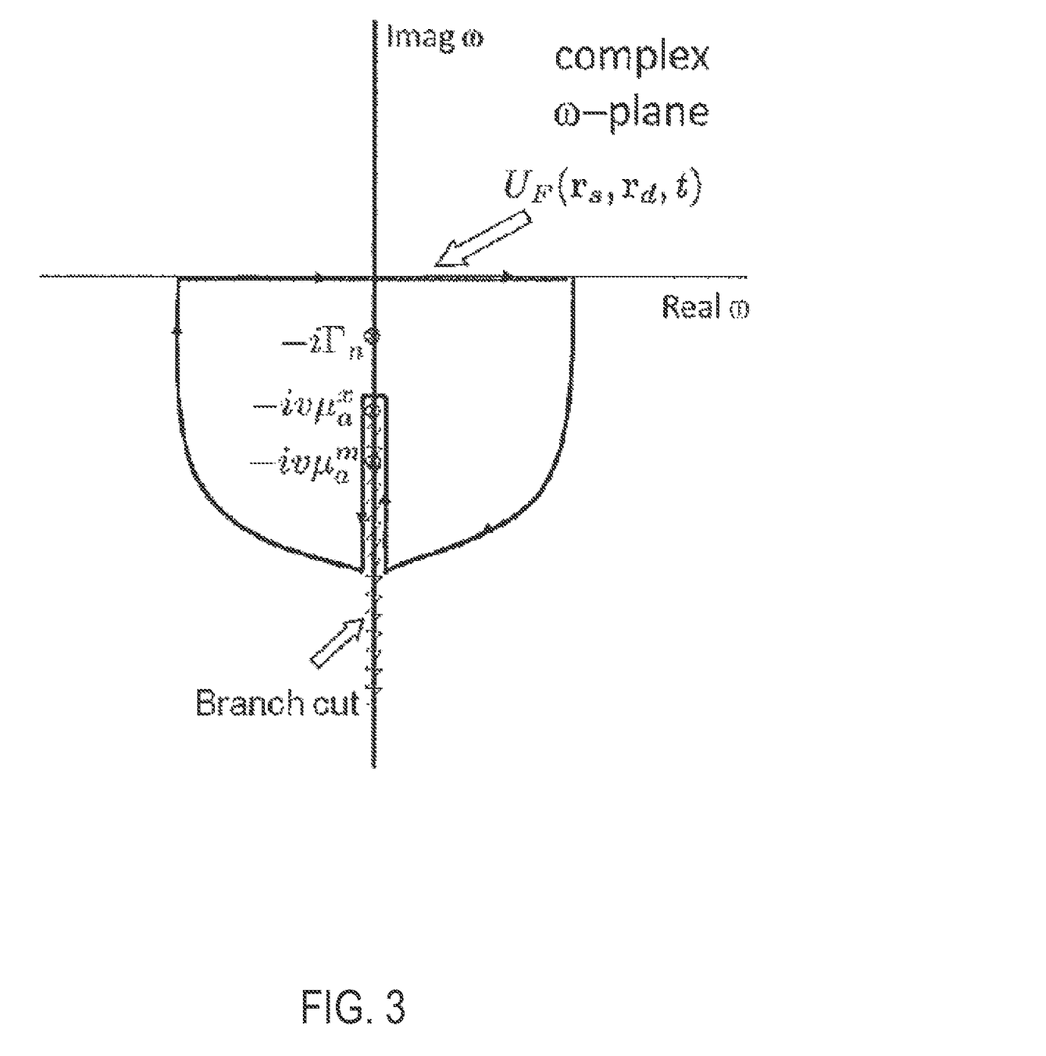
FIG. 3 is a graphical example illustrating a complex plane structure of the diffusion Green's function, in accordance with the present invention.

To understand the present invention further, consider a turbid medium, which may be a biological medium, embedded with fluorophores described by yield distribution $\eta_n(r)$ and corresponding lifetimes $\tau_n = 1/\Gamma_n$. The time-domain fluorescence intensity at position $r_d$ and time t due to excitation by a point source at $r_s$ and at time t=0 is given in the Born approximation by:

$$U_F(r_d, r_s, t) = \sum_n \int_{-\infty}^{\infty} d\omega e^{-i\omega t} \int_V d^3 r \tilde{W}(r_s, r_d, r, \omega) \frac{i\eta_n(r)}{\omega + i\Gamma_n} \quad (1)$$

where $\tilde{W} = \tilde{G}^x(r_s,r,\omega)\tilde{G}^m(r_d,r,\omega)$ is the frequency domain weight function, or sensitivity function, with $G^x$ and $G^m$ as the frequency domain Green's functions for the excitation light from a point source and detector, respectively, to a location r within the biological medium, and the volume integration of Eqn. 1 is over the extent of the medium volume V. Note that $G^x$ and $G^m$ depend on the background optical properties at the excitation $(\mu_a^x, \mu_s^x)$ and emission $(\mu_a^m, \mu_s^m)$ wavelengths. The integrand of Eqn. 1 consists of simple pole singularities at $\omega = -i\Gamma_n$ and branch points at $w = -i v \mu_a^{x,m}$ all located along the negative imaginary axis, as shown in FIG. 3. On applying Cauchy's integral theorem to solve the closed contour in FIG. 3, it is possible to show that $U_F$ separates into two parts, namely the first corresponding to the fluorescence decay terms (arising from the residues at the simple poles) and the other corresponding to the diffuse photon density wave (arising from integration around the branch points). Considering a homogeneous medium, and letting $\mu_a^x = \mu_a^m$ without any loss of generality, it follows that:

$$U_F(r_s, r_d, t) = a_D(r_s, r_d, t)e^{-v\mu_a t} + \sum_n a_{Fn}(r_s, r_d)e^{-\Gamma_n t}. \quad (2)$$

Here $a_D$ is the diffusion term that results from the integration around the branch points and is obtained according to:

$$a_D(r_s, r_d, r, t) = \sum_n \int_V d^3 r \eta_n(r) \frac{1}{\pi} \int_0^\infty d\gamma \frac{\text{Im}[\tilde{W}(r_s, r_d, r, -i\gamma)]}{\gamma + v\mu_a - \Gamma_n} e^{-\gamma t} \quad (3)$$

The fluorescence term consists of the decay amplitudes $a_{Fn}$ for each lifetime $\tau_n$ which are directly related to the yield distribution for that lifetime according to:

$$a_{Fn}(r_s, r_d) = \int_V d^3 r \tilde{W}(r_s, r_d, r; -i\Gamma_n) \eta_n(r). \quad (4)$$

It is worth noting that in Eqn. 3 and Eqn. 4, the $\tilde{W}$ sensitivity function is the same as the one appearing in the standard frequency domain expression in Eqn. 1. For $\Gamma_n < v\mu_a^{x,m}$ the weight function is evaluated at an imaginary frequency that leads to a negative absorption (in Eqn. 3) or a reduced absorption (in Eqn. 4).

Next, the spatial frequency domain in source and detector space is considered, whereby the signal is obtained for input from spatially modulated source of frequency $k_s$ and Fourier transformed for all detector coordinates $r_d$. Eqn. 2 may then be written as a function of the source and detector spatial frequencies, $k_s$ and $k_d$ as follows:

$$\tilde{U}_F(k_s, k_d, t) = \tilde{a}_D(k_s, k_d, t)e^{-v\mu_a t} + \sum_n \tilde{a}_{Fn}(k_s, k_d)e^{-\Gamma_n t}. \quad (5)$$

The present invention recognizes that the term $a_D$ in Eqn. 5. is time dependent and rapidly diminishes for high values of $k_s$ and $k_d$, whereas the second term decays at the same rate (determined by the fluorescence lifetimes $\tau_n = 1/\Gamma_n$), independent of the source $k_s$ or detector spatial frequency $k_d$. The high spatial frequencies at the detection side, or the source (for example, a laser excitation source) side, diminish the diffuse component, while retaining the fluorescent decay component, and therefore control of such spatial frequencies allows for extracting the intrinsic fluorescence decay. Therefore, in some preferred aspects, it may be desirable to apply a spatial frequency filter to the optical data in k-space in order to minimize the diffuse component and extract the intrinsic fluorescence. The choice of an appropriate filter may be determined using information from rate of decay of intrinsic lifetime maps, in dependence of optical properties of the turbid medium. For example, such spatial filter may be a band-pass filter, intended to reduce, minimize, or eliminate signals in a range of desired spatial frequencies.

K-space lifetime maps may then be obtained from fits to the decay portion of the k-space time-domain data. For the case of detector spatial modulation, the spatial time-domain data may be obtained as an inverse FFT of the spatial frequency time-domain data according to:

$$U_F^{filt}(r_s, r_d, t) = \int \frac{d^2 k_d}{(2\pi)^2} f(k_d) \tilde{U}_F(r_s, k_d, t) e^{ik_d \cdot r_d}. \quad (6)$$

where $f(k_d)$ represents a filter function. Subsequently, fits to the asymptotic decays of $U_F^{filt}$ may then be used to recover the true lifetimes.

The above-described systems and methods may be further understood by way of example, offered for illustrative purposes only, and not intended to limit the scope of the present invention in any way. Indeed, various modifications of the invention in addition to those shown and described herein will become apparent to those skilled in the art from the foregoing description and the following example and fall within the scope of the appended claims. For example, certain excitation source and detector arrangements and configurations are presented, although it may be understood that other configurations may be possible, and still considered to be well within the scope of the present invention. Likewise, specific operation or process parameters and methods are recited that may be altered or varied based on variables such as signal amplitude, phase, frequency, wavelength, duration, and so forth.

Example I

Figure 4:
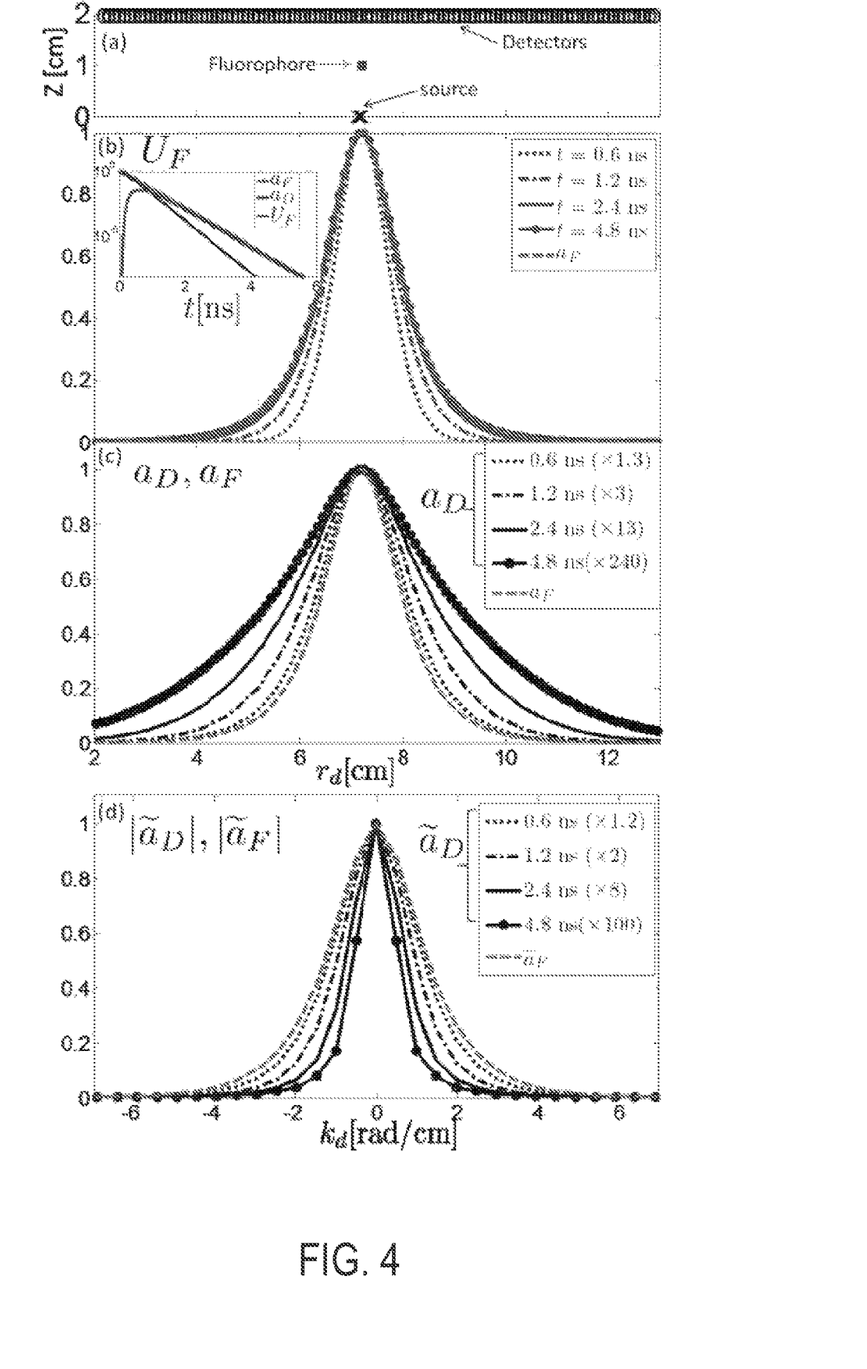
FIG. 4 is a graphical example illustrating a separation of diffuse and fluorescence signal, in accordance with the present invention.

FIG. 4 shows simulations using a diffusive slab model ($\mu_a = 0.2$ cm$^{-1}$, $\mu_s' = 10$ cm$^{-1}$) that includes a single point-like fluorophore (lifetime $\tau = 0.3$ ns) and 256 detectors (CCD pixels), demonstrating the distinct spatiotemporal behavior of $a_D$ and $a_F$ along with the detector k-space transformations for a point illumination case (no modulation at the source). Specifically, the spatial profile $U_F$ ($r_s$, $r_d$, t) expands with time, approaching $a_F$ asymptotically (FIG. 4(b)). FIG. 4(c) shows the separation of $U_F$ ($r_s$, $r_d$, t) into a diffusive contribution, with a spatial distribution, $a_D$, that expands over time, and a time-independent contribution from $a_F$. Correspondingly, FIG. 4(d) shows the spatially transformed $\tilde{U}_F$ decomposed into a spatially narrowing $\tilde{a}_D$ and a stationary $\tilde{a}_F$. The rapid decrease of high spatial frequencies of $\tilde{a}_D$ is similar to that of intrinsic diffuse signals, and suggests that both of these contributions can be minimized in fluorescence signals by a spatial filtering, as described.

Figure 5:
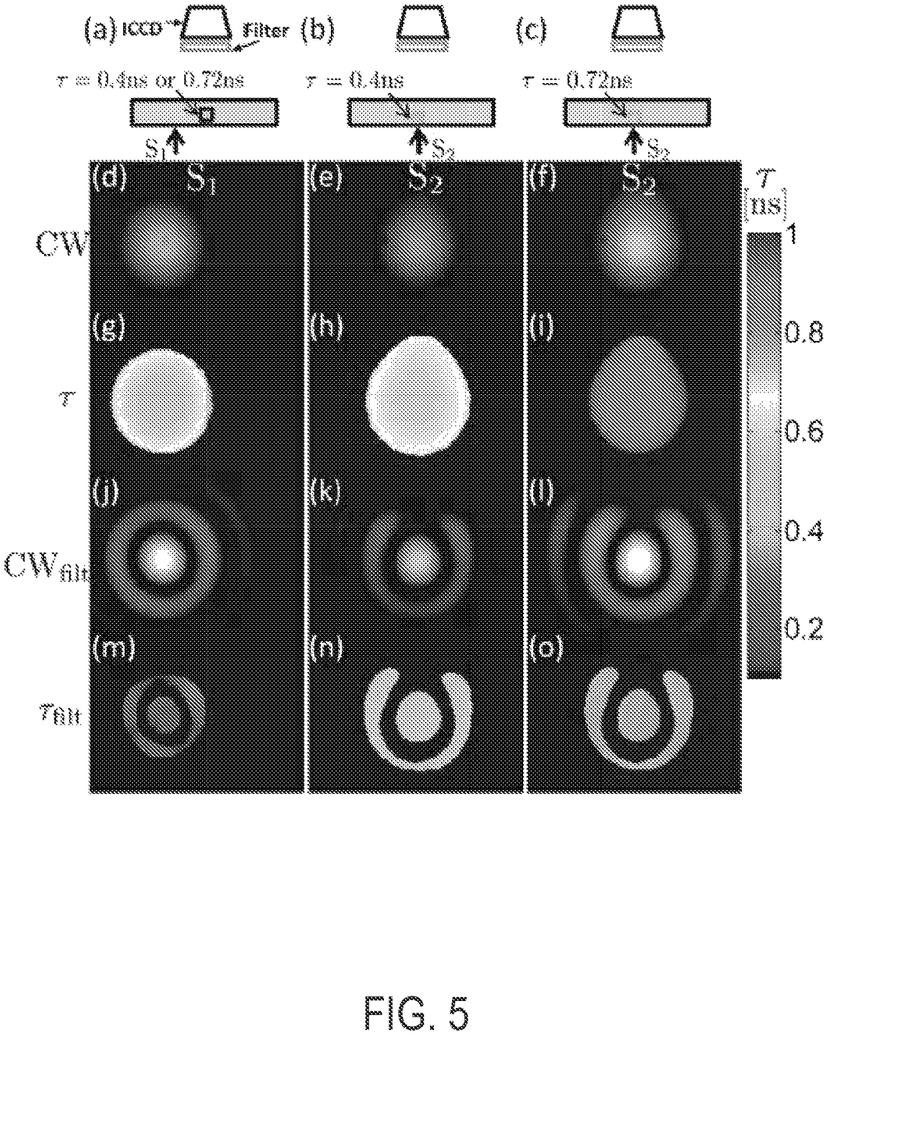
FIG. 5 is a graphical example illustrating fluorescence images and lifetime maps obtained from phantom measurements.

To illustrate that high spatial filtering of time-domain fluorescence signals at the detector end of the sample can allow efficient detection of intrinsic fluorescence lifetimes from turbid media, and the rejection of diffuse excitation leakage, we performed a study using a small tube centrally placed near the bottom of a 1.75 cm thick dish filled with intralipid ($\mu_a \sim 0.02$ cm$^{-1}$, $\mu_s' \sim 22$ cm$^{-1}$). The tube was filled with a 100 µL of 1 µM IRdye800 (LI-COR Biosciences) in either water ($\tau = 0.4$ ns, FIG. 5(b)) or glycerol solvents ($\tau = 0.72$ ns, FIG. 5(c)), and excited in the transmission geometry with a Ti:sapphire laser at 790 nm. Detection was performed with a $\lambda > 800$ nm emission filter attached to an intensified CCD camera (PicostarHR, LAVision, Gmbh; 300 ps gatewidth, 560 V gain, 100 ps steps, 4×4 software binning). The excitation wavelength was intentionally chosen close to the filter pass-band to allow leakage of the diffuse excitation light into the filter, to demonstrate its subsequent elimination by spatial Fourier filtering on the detector side. The full TD data was collected for two source positions 1 cm apart below the phantom, one directly below the fluorescent tube [S2, FIGS. 5(b) and 5(c)], and the other 1 cm away from the tube [S1, FIG. 5(a)]. The CW (integrated time-domain) images [FIGS. 5(d)-5(f)] do not distinguish either source positions or lifetimes in the tube within the phantom. Moreover, the lifetime maps obtained from single-exponential fits to the asymptotic time-domain decay [FIGS. 5(g)-5(i)] do not reflect the true lifetimes of the fluorophores due to the influence of tissue propagation on the time-domain decays and excitation. Note the increase in lifetime from the center of the image toward the edge, due to a larger propagation distance from the source.

The signal for S1 was negligible for 770 nm excitation (not shown), while the lifetime map at 790 nm [FIG. 5(g)] was similar to that without any emission filter (not shown), confirming that the signal for the S1 case is diffuse excitation leakage, which, in the present case, is indistinguishable from the 0.4 ns dye [FIG. 5(h)]. A spatial 2D fast Fourier transform (FFT) in MATLAB (The Mathworks Inc.) was applied to the 2D spatial time-domain CCD images with a threshold set at 3% of the maximum intensity, resulting in the full detector spatial frequency (k-space) time-domain data for all delays. The k-space lifetime maps (FIG. 6) obtained from single-exponential fits to the decay portion of the k-space time-domain data show distinct behavior of the diffuse excitation [FIG. 6(a)] and fluorescence signals [FIGS. 6(b) and 6(c)]; while the k-space lifetime for source S1 (diffuse excitation/leakage) continuously decreases toward higher k's, the lifetime for fluorescence approaches the true fluorophore lifetimes of $0.4\pm0.01$ ns and $0.72\pm0.02$ ns.

Figure 6:
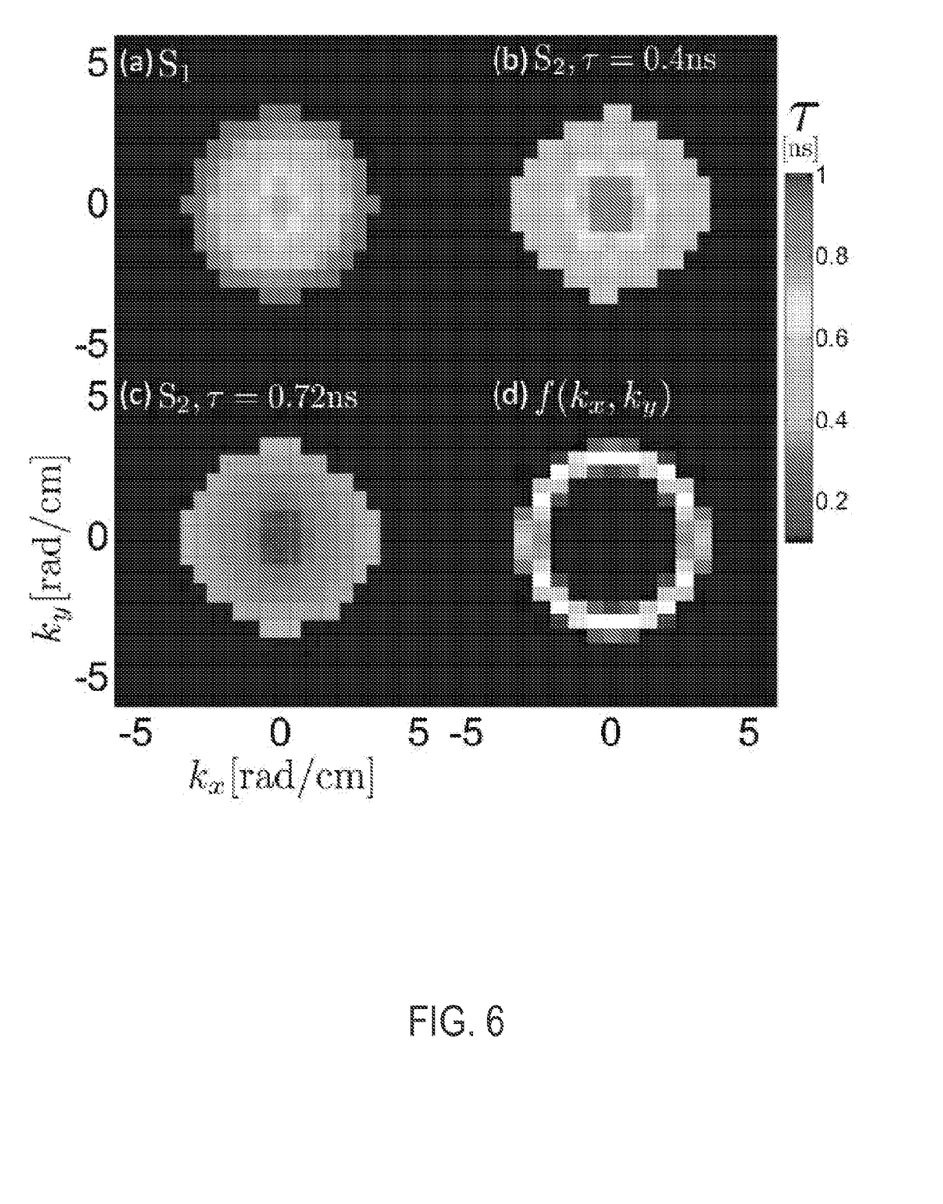
FIG. 6 is a graphical example illustrating lifetime maps in spatial frequency (Fourier) domain corresponding to time-domain data.

It may be desirable to apply a high frequency filter in k-space to extract the intrinsic fluorescence. Here we chose an annular ring [FIG. 6(d)] of the form $f(k_d)=\exp[-(k_x \cos\theta + k_y \sin\theta - R^2)/\sigma^2]$, where $R=|k_d|=\sqrt{k_x^2+k_y^2}$ and $\tan^{-1}[k_y/k_x]$ with $R=3$ rad/cm and $\sigma=1$ rad/cm. This eliminates the diffuse contribution from the low frequencies while also avoiding noisy data at high spatial frequencies.

Figure 7:
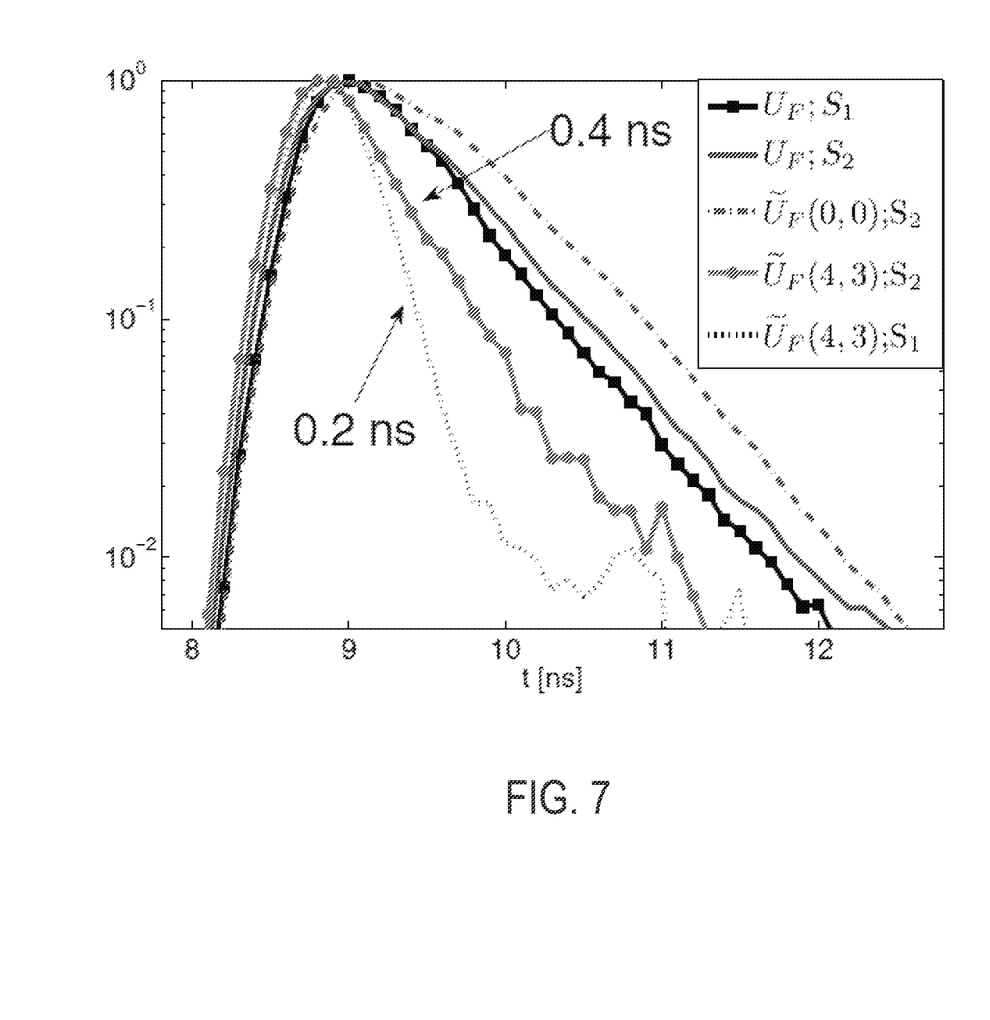
FIG. 7 is a graphical example illustrating raw time-domain data for a detector above a source and spatial Fourier components.

Single-exponential fits to the asymptotic decays of $U_F^{filt}$ of Eqn. 6 [FIGS. 5(m)-5(o)] recover the true lifetimes [FIGS. 5(b) and 5(c)] to within 5% and clearly distinguish the true fluorescence from diffuse excitation leakage [FIG. 5(m)], while the CW components, viz., $\int dt\, U_F^{filt}(t)$ [FIGS. 5(j)-5(l)] do not distinguish the three cases. FIG. 7 shows a sample of raw time data for a detector above the source and the spatial Fourier components for the 0.4 ns case. While the raw time-domain signals are similar for excitation leakage (black) and fluorescence (blue), the true lifetime of $0.4\pm0.01$ ns is recovered for source S2 at $(k_x, k_y)=(4,3)$ rad/cm, whereas the corresponding diffuse excitation leakage for S1 decays at a much shorter rate (0.2 ns). Note the longer lifetime of $\tilde{U}_F(0,0)$ for S2, reflecting the longer lifetimes near the edge of the spatial lifetime map in FIG. 5(h).

In summary, systems and methods are provided for generating and extracting fluorescence lifetimes. In particular, the present invention circumvents confounding factors of typical time-domain (TD) measurements, by employing spatial filtering of time-resolved data obtained using, for example, spatially patterned excitation and detection. In addition, the present invention also makes use of the fact that diffuse components of fluorescence signals decay at a rate that increases with spatial frequency of either a source or detector, while pure fluorescence components decay at intrinsic lifetimes.

As a result, the contribution of the diffuse propagation signal from tissue may be rapidly reduced or eliminated at long times, leaving only a residual fluorescence signal. This allows for both rejection of excitation light leakage (diffuse) and the recovery of the true (intrinsic) lifetime of the fluorophore present in the turbid medium. As such, the present invention enables robust and accurate estimation of both the magnitude (intensity) and lifetime of fluorescence and may widely impact fluorescence imaging applications in biological media.

Specifically it was shown that direct recovery of shorter in vivo lifetimes is possible with TD measurements, by exploiting the separation of diffuse fluorescence into diffuse and pure fluorescent decay terms that exhibits distinct spatiotemporal responses. In the spatial frequency domain (FD), the diffuse term decays at a rate proportional to the spatial frequency, tissue absorption, and scattering (analogous to the temporal propagation of intrinsic diffuse light). However, the decay of the fluorescence term is independent of spatial frequency or optical properties but reflects the characteristic lifetime of the fluorophore in the tissue environment. The fluorescence therefore remains significant at high spatial frequencies, where the diffuse term is rapidly eliminated.

Therefore, the present invention demonstrates that direct detection of lifetimes shorter than the intrinsic diffuse timescales may be achieved. This is not currently possible with existing techniques, which either use continuous wave detection or do not perform spatial Fourier filtering or modulated excitation in the time-domain.

By allowing the use of high spatial frequencies, the approach of the present invention effectively facilitates a reduction of scattering. By contrast, conventional spatial frequency approaches have generally avoided high frequencies since they are rapidly attenuated. However, low frequency signals are more scattered. As such, the present invention capitalizes on the fact that intrinsic fluorescence signals survive high spatial frequencies in the time-domain and thus enables high frequency imaging, which could result in better resolution than currently possible, for example, in fluorescence tomography.

Also, the present invention allows for discrimination of fluorescence from diffuse excitation leakage through emission filters, a common problem encountered in fluorescence imaging. Therefore, the approach offers a powerful way to detect the presence of scattering or excitation leakage in biological lifetime measurements. While only a single lifetime was considered in experiments described, it is conceivable that formalism presented herein is applicable to multiple lifetimes, and can also be extended to tomographic lifetime multiplexing in the spatial Fourier domain.

Additionally, another advantageous feature of the present invention is that the entire spectrum of detector side k-space amplitudes may be obtained from the raw time data with a fast Fourier transform, without the need for complicated modulation techniques on the output (detection) side of the biological sample. Nonetheless, modulated excitation using devices, such as digital light projectors, offers similar advantages at high spatial frequencies, and can offer a powerful new approach for high-throughput tomographic lifetime imaging.

Features suitable for combinations and sub-combinations would be readily apparent to persons skilled in the art upon review of the present application as a whole. The subject matter described herein and in the recited claims intends to cover and embrace all suitable changes in technology.

The invention claimed is:
1. A method for determining fluorescence decay in a biological sample, the method comprising:

acquiring optical signal data from at least one part of a biological sample undergoing fluorescence;

assembling the optical signal data into a set of spatial time-series data;

converting the set of spatial time-series data into a set of spatial frequency time-series data;

applying a spatial filter to the set of spatial frequency time-series data to yield a set of filtered spatial frequency time-series data, the spatial filter configured to separate, from the set of spatial frequency time-series data, fluorescence signals consistent with a non-diffuse component;

converting the set of filtered spatial frequency time-series data into a set of filtered spatial time-series data;

determining, using the filtered spatial time-series data, a fluorescence signature consistent with fluorescence decay of at least one fluorophore in the biological sample; and generating a report indicative of the fluorescence signature corresponding to the biological sample.

2. The method of claim 1, the method further comprises creating an excitation in the at least one part of biological sample using a point-like light source.

3. The method of claim 1, the method further comprises creating an excitation in the at least one part of biological sample using a pulsed light source.

4. The method of claim 1, the method further comprises creating an excitation in the at least one part of biological sample using a spatially modulated light source.

5. The method of claim 1, wherein assembling the set of spatial time-series data further comprises performing a threshold processing using a maximum intensity of signals associated with the optical signal data.

6. The method of claim 1, wherein converting the set of spatial time-series data includes performing a Fourier transform for a plurality of time points.

7. The method of claim 1, wherein the spatial filter is dependent upon a fluorescence decay profile determined by optical properties of the biological sample.

8. The method of claim 1, wherein the spatial filter is a band-pass filter that minimizes fluorescence signals described by spatial frequencies consistent with a diffuse component.

9. The method of claim 1, wherein converting the set of filtered spatial frequency time-series data includes performing an inverse Fourier transform for a plurality of time points.

10. The method of claim 1, the method further comprises performing a curve fitting process, using the filtered spatial time-series data, to determine the fluorescence decay of the at least one fluorophore.

11. The method of claim 1, wherein the report includes at least one lifetime map obtained using the fluorescence decay of the at least one fluorophore.

12. The method of claim 1, wherein the fluorescence decay of the at least one fluorophore is shorter than an intrinsic temporal response of a diffuse medium including the at least one part of the biological sample undergoing fluorescence.

13. A system for determining fluorescence decay in a biological sample, the system comprising:

an input designed to receive optical signal data from at least one part of a biological sample undergoing fluorescence;

at least one processor configured to:
assemble the optical signal data into a set of spatial time-series data;

convert the set of time-series data into a set of spatial frequency times-series data;

apply a spatial filter to the set of spatial frequency time-series data to yield a set of filtered spatial frequency time-series data, the spatial filter configured to separate, from the set of spatial frequency time-series data, fluorescence signals consistent with a non-diffuse component;

convert the set of filtered spatial frequency time-series data into a set of filtered spatial time-series data;

determine, using the filtered spatial time-series data, a fluorescence signature consistent with fluorescence decay of at least one fluorophore in the biological sample; and generate a report indicative of the fluorescence signature corresponding to the biological sample.

14. The system of claim 13, the system further comprising an excitation source for creating an excitation in the at least one part of biological sample.

15. The system of claim 14, the excitation source configured to create an excitation defined by at least one of a point-like light excitation, a pulsed light excitation, and a spatially modulated excitation.

16. The system of claim 13, wherein the at least one processor is further configured to perform a threshold processing using a maximum intensity of signals associated with the optical signal data.

17. The system of claim 13, wherein the at least one processor is further configured to perform a Fourier transform, using the set of spatial time-series data, for a plurality of time points.

18. The system of claim 13, wherein the spatial filter is dependent upon a fluorescence decay profile determined by optical properties of the biological sample.

19. The system of claim 13, wherein the spatial filter is a band-pass filter that minimizes fluorescence signals described by spatial frequencies consistent with a diffuse component.

20. The system of claim 13, wherein the at least one processor is further configured to perform an inverse Fourier transform, using the set of filtered spatial frequency time-series data, for a plurality of time points.

21. The system of claim 13, wherein the at least one processor is further configured to perform a curve fitting process, using the filtered spatial time-series data, to determine the fluorescence decay of the at least one fluorophore.

22. The system of claim 13, wherein the report includes at least one lifetime map obtained using the fluorescence decay of the at least one fluorophore.

23. The system of claim 13, where the fluorescence decay of the at least one fluorophore is shorter than an intrinsic temporal response of a diffuse medium including the at least one part of the biological sample undergoing fluorescence.

24. A method for determining fluorescence decay in a biological sample, the method comprising:

assembling a set of spatial time-series data using optical signals acquired from a biological sample having a plurality of fluorophores;

converting the set of spatial time-series data into a set of spatial frequency time-series data;

applying a filter to the set of spatial frequency time-series data to yield a set of filtered spatial frequency time-series data, the filter configured to separate, from the set of spatial frequency time-series data, fluorescence signals consistent with a non-diffuse component;

converting the set of filtered spatial frequency time-series data into a set of filtered spatial time-series data;

determining, using the filtered spatial time-series data, a fluorescence signature consistent with fluorescence decay of at least one fluorophore in the plurality of fluorophores; and generating a report indicative of the fluorescence signature corresponding to the biological sample.

25. The method of claim 24, the method further comprises creating an excitation in the biological sample using a point-like light source.

26. The method of claim 24, the method further comprises creating an excitation in the biological sample using a pulsed light source.

27. The method of claim 24, the method further comprises creating an excitation in the biological sample using a spatially modulated light source.

28. The method of claim 24, wherein assembling the set of spatial time-series data further comprises performing a threshold processing using a maximum intensity of signals associated with the optical signals acquired from the biological sample.

29. The method of claim 24, wherein converting the set of spatial time-series data includes performing a Fourier transform for a plurality of time points.

30. The method of claim 24, wherein the filter is dependent upon a fluorescence decay profile determined by optical properties of the biological sample.

31. The method of claim 24, wherein the filter is a band-pass filter that minimizes fluorescence signals described by spatial frequencies consistent with a diffuse component.

32. The method of claim 24, wherein converting the set of filtered spatial frequency time-series data includes performing an inverse Fourier transform for a plurality of time points.

33. The method of claim 24, the method further comprises performing a curve fitting process, using the filtered spatial time-series data, to determine the fluorescence decay of the at least one fluorophore.

34. The method of claim 24, wherein the report includes at least one lifetime map obtained using the fluorescence decay of the at least one fluorophore.

35. The method of claim 24, where the fluorescence decay of the at least one fluorophore is shorter than an intrinsic temporal response of a diffuse medium including the biological sample.

* * * * *